(12) United States Patent
Adden et al.

(10) Patent No.: US 8,623,840 B2
(45) Date of Patent: Jan. 7, 2014

(54) METHODS AND COMPOSITIONS FOR INDUCING SATIETY

(75) Inventors: Roland Adden, Hannover (DE); William H. Anderson, Midland, MI (US); Britta Huebner, Uetze (DE); Matthias Knarr, Nienburg (DE)

(73) Assignee: Dow Global Tchnologies LLC, Midland, MI (US)

( * ) Notice: Subject to any disclaimer, the term of this patent is extended or adjusted under 35 U.S.C. 154(b) by 69 days.

(21) Appl. No.: 13/095,414

(22) Filed: Apr. 27, 2011

(65) Prior Publication Data

US 2011/0269711 A1 Nov. 3, 2011

Related U.S. Application Data

(60) Provisional application No. 61/329,396, filed on Apr. 29, 2010.

(51) Int. Cl.
*A61K 31/717* (2006.01)

(52) U.S. Cl.
USPC .......................................................... 514/57

(58) Field of Classification Search
USPC .......................................................... 514/57
See application file for complete search history.

(56) References Cited

U.S. PATENT DOCUMENTS

| | | | |
|---|---|---|---|
| 4,042,719 | A | 8/1977 | Zimmermann nee Ignacz et al. |
| 5,462,742 | A | 10/1995 | Bogentoft et al. |
| 6,235,893 | B1 | 5/2001 | Reibert et al. |
| 7,368,431 | B2 | 5/2008 | Severin et al. |
| 7,422,764 | B2 | 9/2008 | Navarro y Koren et al. |
| 2005/0233045 | A1 | 10/2005 | Aldred et al. |
| 2007/0087038 | A1 | 4/2007 | Richardson et al. |

FOREIGN PATENT DOCUMENTS

| | | |
|---|---|---|
| DE | 10160409 | 6/2003 |
| GB | 745926 | 3/1956 |

OTHER PUBLICATIONS

Howarth et al., Fermentable and nonfermentable fiber supplements did not alter hunger, satiety or body weight in a pilot study of men and women cosuming selfselcted diets. J. Nutr. 133:3141-3144, 2003.*
Kwiatek et al., Quantification of distal antral contractile motility in healthy human stomach with magnetic resonance imaging. J. Magn. Reson. Imaging 24:1101-1109, 2006.*
Burton et al. Relatioship of gastric emptying and vol. changes after a solid meal in humans. Am J Physiol Gastrointest Liver Physiol 289:G261-G266, 2005.*
Furnass; "Too Many Calories"; Letter to the editor; The Lancet; 1960; 263-264.
Badham; "Methylcellulose for Obesity"; Letters to the editor; The Lancet; 1953; 1316.
Norton et al.; "Fluid gels, mixed fluid gels and satiety"; Food Hydrocolloids; 2006; 20; 229-239; Elsevier.
Yudkin, The Lancet, 1959, 274, 7112, 1135-1138.
Yudkin, The Lancet, 1960, 275, 7139, 1431.
Beisel et al, DE10160409(A1), Abstracts from two sources, Jun. 18, 2003.

* cited by examiner

Primary Examiner — Wu-Cheng Winston Shen
Assistant Examiner — Yih-Horng Shiao

(57) ABSTRACT

The present invention provides a medicament or food supplement, that when ingested by an individual, forms a gel mass in the individual's stomach, said gel mass consisting essentially of methylcellulose and water, as well as methods for inducing satiety, reversibly reducing stomach void volume, and reducing caloric intake in an individual.

13 Claims, No Drawings

METHODS AND COMPOSITIONS FOR INDUCING SATIETY

CROSS-REFERENCE TO RELATED APPLICATIONS

This application claims benefit of priority from U.S. Provisional Patent Application No. 61/329,396, filed Apr. 29, 2010, which application is incorporated by reference herein in its entirely.

FIELD

The present invention relates to nutrition generally, and specifically to methods and compositions for inducing satiety.

BACKGROUND

In nutritional terms, satiety is a complex response, involving both an individual's emotional and physical perception of whether or not they have ingested enough. Satiety can be observed as a reduction of appetite immediately following consumption, or as a reduction of food intake at the next meal. For purposes of this specification, "satiety" refers to a net reduction of caloric intake by an individual.

As can be appreciated, control of satiety is most relevant in cases where an individual consumes more calories than are necessary. Inducing satiety can be useful for causing a reduced caloric intake, i.e., for aesthetic purposes (i.e., as a slimming aid for weight loss or weight management) or for medical treatment (for example, for treating obesity).

Various strategies for inducing satiety have been developed. One method involves inducing a nutritional response by eating a high protein diet comprising, for example whey protein. The disadvantage of using this strategy is the additional calories that are consumed in order to achieve satiety. Another strategy includes providing an alginate material that can be crosslinked with a co-administered calcium ion to form a globule that induces a feeling of fullness. However, this is disadvantageous for several reasons. First, the calcium ion must be administered within a certain time of ingestion of the alginate in order to achieve gelation, thereby risking a complete lack of efficacy if the individual is delayed or distracted. Accordingly, two-step processes are conventionally considered a serious drawback for self-administration of actives. Second, the alginate material will only gel under certain pH conditions—thus, efficacy can be impaired or even destroyed by co-ingested foods or existing stomach contents.

Therefore, what is needed is a satiety inducing composition with a gelation mechanism that does not require a separate crosslinker, and that is not pH dependent.

SUMMARY

In one embodiment, the present invention provides a medicament or food supplement for reducing caloric intake, that when ingested by an individual, forms a gel mass in the individual's stomach, said gel mass consisting essentially of methylcellulose.

In another embodiment, the present invention provides a method for inducing satiety in an individual, comprising administering to said individual, a methylcellulose that gels in the individual's stomach.

In yet another embodiment, the present invention provides a method for reversibly reducing stomach void volume in an individual, comprising administering to said individual, a methylcellulose that gels in the individual's stomach.

In yet another embodiment, the present invention provides a method for distending an individual's stomach, comprising administering to said individual, a methylcellulose that gels in the individual's stomach.

In yet another embodiment, the present invention provides a method of reducing caloric intake in an individual, comprising administering to said individual, a liquid comprising a methylcellulose that gels in the individual's stomach.

DETAILED DESCRIPTION

Cellulose has a polymeric backbone repeating structure of anhydroglucose units joined by 1-4 linkages. Each anhydroglucose unit contains hydroxyl groups at the 2, 3, and 6 positions. Substitution of these hydroxyls creates cellulose derivatives. For example, treatment of cellulosic fibers with caustic solution, followed by a methylating agent, yields cellulose ethers substituted with one or more methoxy groups. If not further substituted with other alkyls, this cellulose derivative is known as methylcellulose.

Methylcellulose typically has a weight average molecular weight of at least 12 kDa, preferably at least 15 kDa. A rough description of a particular methylcellulose can be given by its "DS," a term that refers to the average degree of methoxyl substitution per anhydroglucose unit of the cellulose derivative. Theoretically, methylcellulose can have a DS of about 1 to about 3, but in practice, methylcellulose typically has a DS of about 1.47 to about 2.2.

Conventionally, methylcellulose has been found to be very useful in a variety of applications, providing thickening, freeze/thaw stability, lubricity, moisture retention and release, film formation, texture, consistency, shape retention, emulsification, binding, gelation, and suspension properties. However, conventional methylcellulose does not result in a reduction of energy intake (induce satiety), as shown in the accompanying examples.

One unusual property of methylcellulose is that it is known to exhibit reverse thermal gelation, in other words, methylcellulose gels at warmer temperatures and forms a liquid at cooler temperatures. Most grades of methylcellulose gel at around 50° C. to 60° C. A grade of methylcellulose that gels at a relatively low temperature, 38° C. to 44° C., is generally available under the tradename METHOCEL SG or SGA (The Dow Chemical Company). No grades of commercially available methylcellulose gel at temperatures as low as an individual's normal body temperature, however, U.S. Pat. No. 6,235,893, the entirety of which is incorporated by reference herein, teaches methylcelluloses that gel as low as 31° C.

In one embodiment, the present invention provides a medicament or food supplement for reducing caloric intake, that when ingested by an individual, forms a gel mass in the individual's stomach, said gel mass consisting essentially of methylcellulose and water. "Individual" refers to an animal, preferably a mammal, more preferably a human. "Gel mass" refers to a colloidal system consisting of a solid and a substantial quantity of a liquid with properties of a soft solid. Gelation refers to the process of formation of a gel mass from a solution or formulation. In one embodiment, the solid portion consists essentially of methylcellulose. The fact that pre-ingested food particles may become entrapped during gelation does not depart from the spirit of the invention.

In a preferred embodiment, the gelation is temperature-activated by the individual's body temperature, i.e., no crosslinker is required. In a preferred embodiment, the present methylcellulose is made according to the processes described in U.S. Pat. No. 6,235,893. U.S. Pat. No. 6,235,893 described lower gelation temperature as a desired and preferred but non-essential feature, (col. 3, lines 32-33). In contrast, however, as can be appreciated, a gelation temperature at or below the individual's body temperature is a critical feature for the present application in embodiments where the gelation is temperature-activated by the individual's body temperature.

It is contemplated that, in one embodiment, the medicament or food supplement is useful for treating gastric ulcers, gastro-esophageal reflux disease, or obesity. In a preferred embodiment, the medicament or food supplement is useful for treating obesity. In another embodiment, the medicament is useful for indications that require gastric space to be occupied for at least 60 minutes, preferably at least 120 minutes, more preferably, at least 180 minutes, and most preferably, at least 240 minutes.

Alternatively, in another embodiment, the food supplement is useful as a slimming, or weight loss, aid, such as in a non-obese individual for aesthetic reasons, such as weight management.

Alternatively, in another embodiment, the food supplement is useful for reducing total daily caloric intake.

In another embodiment, the present invention provides a method for inducing satiety in an individual, comprising administering to said individual, a methylcellulose that gels in the individual's stomach. As shown in the accompanying examples, the present invention demonstrates induction of satiety (measured by a reduction in energy intake), and has been shown to gel in the stomach in humans and rodents.

In one embodiment, the methylcellulose is combined with a protein such as those present in dairy products for example whey protein, lacto albumin, or casein and the like which increases the gel fracture force by at least preferably 10%, more preferably 20% and most preferably 50%. In a preferred embodiment, the gelation is temperature-activated by the individual's body temperature, i.e., no crosslinker is required.

Preferably, the methylcellulose enters the stomach in liquid form. For purposes of this specification, "liquid" refers to any substance that takes the shape of its container at room temperature. Non-limiting examples include yogurts, smoothies, drinks, shakes, fruit beverages, beverage shots, sports drinks, and other solutions, as well as emulsions, including ice cream, cream cheese, ketchup, spreads, dips, picante, salad dressing, homogenized milk, mayonnaise, gravies, puddings, soups, and sauces. It is understood that the temperature of the liquid should not be higher than the gelation temperature of the methylcellulose.

In practice, the liquid should contain sufficient methylcellulose to induce the proper rate of gelation and strength of gel, as well as to achieve an initial viscosity (before imbibition) of at least 600 mPa's, preferably at least 1000 mPa's when measured at a shear rate of $10 \sec^{-1}$. Accordingly, concentrations of methylcellulose in the liquid may understandably vary. Generally, a range of, for example, at least 0.2 weight percent methylcellulose to 2.1 weight percent methylcellulose in the liquid is contemplated. Similarly, for a human, the individual should consume more than three, preferably four grams of methylcellulose. However, not to be bound by any theory it is believed that the gel fracture force and volume of the gel mass in vivo are the primary considerations. Administration of a 300 mL volume of liquid of a 2% solution, a 1.5% solution, and even a 1.0% solution are contemplated. Alternatively administration of a 2% solution in a 200 mL volume is possible.

In one embodiment, the individual should abstain from imbibing further liquids until the methylcellulose has an opportunity to gel.

In one embodiment, the methylcellulose substantially gels in at least 45 minutes, preferably in at least 20 minutes, and more preferably, in at least 15 minutes, upon entering the stomach.

In vitro gel fracture force of the gelled liquid measured after conditioning the sample at 39.5° C. for 1 hour is a proxy for in vivo gelling. A gel fracture force of at least 1.5 N is preferred, more preferably at least 4N, and most preferably at least 6 N.

In yet another embodiment, the present invention provides a method for reversibly reducing stomach void volume in an individual, comprising administering to said individual, a methylcellulose that gels in the individual's stomach. Not to be bound by any theory, formation of the gel mass causes distention of the stomach wall to occur resulting in a biological signal of satiety and leaving less of the individual's stomach volume available for food. In a preferred embodiment, the methylcellulose has a gel point below the individual's body temperature.

In yet another embodiment, the present invention provides a method of reducing caloric intake in an individual, comprising administering to said individual, a liquid comprising a methylcellulose that gels in the individual's stomach. In this embodiment, the methylcellulose is preferably administered at least 45 minutes, preferably at least 20 minutes, and more preferably, at least 15 minutes, before the individual eats. Preferably, the individual is a human, and the individual consumes a solution containing at least more than three, preferably at least four grams of methylcellulose.

It is understood that the individual's stomach eventually breaks down the gel mass, allowing it to pass from the stomach into the upper gastrointestinal tract. Naturally occurring mechanisms that breakdown the gel mass include physical disruption by stomach motility and dilution with gastric juices (and consequent reversion to a liquid form). Animal studies indicate degradation of gel mass occurs preferably within 2 hours, more preferably within 4 hours, and most preferably within 6 hours.

Methods of making methylcellulose are described in detail in U.S. Pat. No. 6,235,893. Generally, cellulose pulp is treated with a caustic, for example an alkali metal hydroxide. Preferably, about 1 to about 3.5 mol NaOH per mole of anhydroglucose units in the cellulose is used. Uniform swelling and alkali distribution in the pulp is optionally controlled by mixing and agitation. The rate of addition of aqueous alkaline hydroxide is governed by the ability to cool the reactor during the exothermic alkalization reaction. In one embodiment, an organic solvent such as dimethyl ether is added to the reactor as a diluent and a coolant. Likewise, the headspace of the reactor is optionally purged with an inert gas (such as nitrogen) to control oxygen-catalyzed depolymerization of the cellulose ether product. In one embodiment, the temperature is maintained at or below about 45° C.

A methylating agent, such as methyl chloride or dimethyl sulfate, is also added by conventional means to the cellulose pulp, either before, after, or concurrent with the caustic, generally in an amount of about 1.5 to about 4 mol methylating agent per mole of anhydroglucose units in the cellulose. Preferably, the methylating agent is added after the caustic. Once the cellulose has been contacted with caustic and methylating agent, the reaction temperature is increased to about 75° C. and reacted at this temperature for about half an hour.

In a preferred embodiment, a staged addition is used, i.e., a second amount of caustic is added to the mixture over at least 60 minutes, preferably at least 90 minutes, while maintaining the temperature at least about 55° C., preferably a least 65° C., more preferably at least 80° C. Preferably, about 2 to about 4 mol caustic per mole of anhydroglucose units in the cellulose is used. A staged second amount of methylating agent is added to the mixture, either before, after, or concurrent with the caustic, generally in an amount of about 2 to about 4.5 mol methylating agent per mole of anhydroglucose units in the cellulose.

The cellulose ether is washed to remove salt and other reaction by-products. Any solvent in which salt is soluble may be employed, but water is preferred. The cellulose ether may be washed in the reactor, but is preferably washed in a separate washer located downstream of the reactor. Before or after washing, the cellulose ether may be stripped by exposure to steam to reduce residual organic content.

The cellulose ether is dried to a reduced moisture and volatile content of preferably about 0.5 to about 10.0 weight percent water and more preferably about 0.8 to about 5.0 weight percent water and volatiles based upon the weight of cellulose ether. The reduced moisture and volatiles content enables the cellulose ether to be milled into particulate form. The cellulose ether is milled to particulates of desired size. If desired, drying and milling may be carried out simultaneously.

EXAMPLES

The following examples are for illustrative purposes only and are not intended to limit the scope of the present invention. All percentages are by weight unless otherwise specified.

Example 1

Exemplary low temperature gelling methylcellulose to be used according to the present invention was made according the techniques described in U.S. Pat. No. 6,235,893, with conditions selected so that the resulting product initiates gel mass formation below about 37° C., e.g., roughly the normal body temperature of many mammals, including mice, hamsters, and humans. This methylcellulose is hereinafter referred to as Batch A.

To obtain a 2% aqueous solution of Batch A, 3 g of milled, ground, and dried Batch A are added to 147 g of tap water (temperature 20-25° C.) at room temperature while stirring with an overhead lab stirrer at 500 rpm with 3-wing (wing=2 cm) blade stirrer. The solution is then cooled to about 1.5° C. and the speed of the stirrer is reduced stepwise: 500 rpm for 15 min, then 400 rpm for 10 min, then 200 rpm for 10 min, and then 100 rpm for 5 h. The solution is then stored over night at about 0.5-about 1° C. Prior to use or analysis, the solution is stirred for 15 min at 100 rpm in an ice bath.

Example 2

Solutions of Batch A were prepared substantially as described above in Example 1, except the solution was not stirred in an ice bath and the solution was not stirred for 15 min before use. Sample concentrations of 0.70, 0.90, 1.10, 1.30, 1.50 and 1.70 weight-volume % were prepared. 1.2 mL of liquid solution (about 7.5 mL/kg of body weight) of each concentration was fed by gavage in triplicate to rats that had been fasted for 16 hours before testing (water provided ad libitum). After 45 min, the rats were sacrificed and dissected to observe the stomach contents. Descriptions are reported in Table 1:

TABLE 1

| Concentration | Stomach Content Observation |
| --- | --- |
| 0.7% wt/vol | No gel |
| 0.9% wt/vol | Small soft gel |
| 1.1% wt/vol | Small soft gel |
| 1.3% wt/vol | Small soft gel |
| 1.5% wt/vol | Large firm gel |
| 1.7% wt/vol | Stomach shaped gel |

"No gel" indicates a liquid flowed from the stomach. "Small soft gel" indicates relatively small, relatively soft, nonflowing gel masses were observed surrounded by liquid. "Large firm gel" indicates relatively large, relatively firm, nonflowing gel masses were observed. Interestingly, the 1.7% concentration developed a gel mass that substantially filled the rats' stomachs. The gel mass maintained the shape of the rat's stomach after being removed from the stomach tissue.

Example 3

Solutions of Batch A were prepared substantially as described above in Example 1, except the solution was not stirred in an ice bath. Sample concentrations of 0.70, 0.90, 1.10, 1.30, 1.50 and 1.70 weight-volume % were prepared.

To test the viscosity, solutions were measured in a flow curve experiment over a shear rate region of $0.1\text{-}1000\ s^{-1}$ at 5° C. using an Anton Paar Physica MCR 501 or Haake RS600 rheometer with peltier system and cone and plate geometries (CP50-1/TG) with 5 measurement points each decade (logarithmic scale).

To test the gel fracture force the gel mass was characterized with a Texture Analyzer (Stable Micro Systems, Surrey, UK) with a force cell of 5 kg.

6.5 g of the test solutions were placed into each of 6 20 mL syringes (NORM-JECT Luer) which have the end cut off above the needle port. The 6 syringes are stored in a rack where the open ends of the syringes are covered with a glass plate. This rack is then placed into a 39.5° C. water bath for 1 h and during this time gels formed in the syringes.

The rack was removed from the water bath and the gels were carefully removed from the syringes by pressing the piston. These gel masses (height=20 mm, diameter=20 mm) were then placed below the probe of the texture analyzer (Teflon Plate with a diameter of 50 mm). This probe was then lowered near to the surface of the gel bodies and the compression test was started (Test speed=10 mm/s; Trigger force=0.5 g; Distance=18 mm). The gel fracture force is taken from the plot of force in [N] vs. distance [mm] as the maximum in force values. The measurements were done at ambient temperature in 2-3 min after the removal of the rack from the water bath. Results are reported in Table 2:

TABLE 2

| Concentration | Viscosity [mPa s] | Gel Fracture Force [N] |
| --- | --- | --- |
| 0.7% wt/vol | Not determined | No measurable gel |
| 0.9% wt/vol | Not determined | No measurable gel |
| 1.1% wt/vol | 750 | 0.5 |
| 1.3% wt/vol | 1300 | 1.1 |
| 1.5% wt/vol | 2000 | 1.5 |
| 1.7% wt/vol | 3000 | 2.4 |

Example 4

To determine if Batch A had a statistically significant effect on satiety as compared to conventional methylcellulose, a human clinical study was commissioned. The study design was reviewed by a certified Institutional Review Board and was conducted in accordance with International Conference on Harmonization/Good Clinical Practice standards.

Human satiety trials results are known to be affected by taste perceptions. Mint chocolate flavored formulations were prepared in order to make the samples palatable. Comparative Batch Z, a conventional non-gelling methylcellulose was selected to have a closely matched initial viscosity with Inventive Batch A. Formulations are reported in Table 3, in weight percent:

TABLE 3

|  | Comparative Batch X | Comparative Batch Z | Inventive Batch 1 |
|---|---|---|---|
| Xanthan | 0.1 | — | — |
| METHOCEL A4M methylcellulose | — | 2 | — |
| Batch A methylcellulose | — | — | 2.0 |
| Cocoa | 2.0 | 2.0 | 2.0 |
| Sweetener | 0.24 | 0.24 | 0.24 |
| Mint Oil | 0.017 | 0.017 | 0.017 |
| Water | 97.65 | 95.75 | 95.75 |

$T_{gel}$ for METHOCEL A4M methylcellulose is 55° C.
$T_{gel}$ for Batch A methylcellulose is 28° C.

To test the gelation temperature, solutions were measured in a temperature sweep experiment using an Anton Paar Physica MCR 501 or Haake RS600 rheometer with peltier temperature control system in oscillation shear flow. A parallel plate (PP-50) with a measurement gap of 1 mm was used. The geometry was covered with a further metal ring (inner diameter of 65 mm, width of 5 mm, height of 15 mm) around the geometry and the outer surface of the solution was covered with a paraffin oil. The measurements were performed at a constant frequency of 2 Hz. and a constant strain (deformation) of 0.5% from 5° C. to 85° C. with a heating rate of 1° K/min. The storage modulus G', which is obtained from the oscillation measurements, represents the elastic properties of the solution (during the gelation process of methylcellulose, G' increases). The loss modulus G", which is obtained from the oscillation measurements, represents the viscous properties of the solution. The gelation temperature is determined as the temperature at the cross over of the G' and G" curves.

These aqueous flavored solutions were estimated to have a caloric content of less than 5 kcal per 300 mL dose due to the caloric contribution of the flavorings and sweetener.

Four groups were created, consuming 300 mL Batch X, 300 mL Batch Z, 300 mL Batch 1, and 150 mL Batch 1. For the control batches, a 25 kg batch size was used during preparation and the batches were filled into 450 mL size pots (300 g/pot) directly after cooling and stored overnight at 3° C. The samples were then frozen in the pots and stored at −20° C. The samples required for consumption were removed from the freezer and defrosted over 24 h at 7° C. prior to consumption.

For the test batch a 30 kg batch size was used. The batch was filled into 4 L plastic containers (2.4 kg per container) and the containers slowly rotated overnight at 3° C. on a conveyer belt to help degas the samples and ensure full hydration of the methyl cellulose. The samples were then frozen and stored at −20° C. Prior to consumption a 2.4 kg sample in a 4 L container was defrosted and used to provide participants with either 300 mL or 150 mL of the assigned batch sample. The sample was defrosted over two nights with 28 h rotating at 7° C. followed by approximately 16 h rotating at 3° C.

A population of 32 participants was recruited according to the following criteria: age at start of the study, between or equal to 20 and 60; Body Mass Index (BMI) between or equal to 18.5 and 25 kg/m$^2$, apparently healthy (measured by questionnaire, no reported current or previous metabolic diseases or chronic gastrointestinal disorders), good reported dietary habits (no medically prescribed diet, no slimming diet, accustomed to eating 3 meals a day), no blood donation during the study, less than or equal to 10 hours per week of exercise/sporting activities, less than or equal to 21 (female) or 28 (male) alcoholic beverages a week. Potential participants were excluded for smoking, allergies or lactose intolerance, dislike, allergy or intolerance to experimental products, possible eating disorder (measured by SCOFF questionnaire), reported lactating (or lactating<6 weeks ago), pregnant (or pregnant<3 months ago) or wish to become pregnant during the study, reported medical treatment that might affect eating habits/satiety, or reported participation in another biomedical trial 1 month or less before the start of the study.

The four samples were tested using a William's squared randomized double blind cross-over design. Over a period of four weeks, each participant visited the test facility on four occasions (each a "study day") to complete the study with one week wash-out period between each study day.

Participants were asked to eat as normal on the evening before the study day, but to stop eating at 20.00 hours, and to record everything they consumed between 18.00 and 20.00 hours. Drinking after 20.00 hours was allowed, but restricted only to water or black tea/coffee with no sugar and no milk. Participants were also asked to abstain from alcohol and vigorous exercise for 24 hours prior to each study day, and to refrain from drinking any liquids for 1 hour before the start of the study day.

On the study day, participants were instructed to arrive at 08.45 hours. Ten minutes before consumption of breakfast, participants completed baseline ratings for satiety feelings. At 09.00 hours, a breakfast standardized for each participant's weight was provided consisting of cornflakes (0.67 g/kg) and semi-skimmed milk (2.5 g/kg). Participants were seated in booths to isolate them and were instructed not to talk to each other. Participants were given 15 minutes to eat the breakfast. Immediately post consumption, questionnaires on satiety were completed, after which the participants were free to leave the booths.

Questions on satiety were asked every 30 minutes until immediately prior consumption of the assigned batch sample. Thereafter they received the assigned batch sample and were given fifteen minutes to consume it. Immediately post consumption, questionnaires on satiety and liking were completed.

Non-caloric drinks (water, tea/coffee without milk/sugar) were allowed during the study day (however the participants were asked to abstain from drinking for 45 minutes before and after consumption of the assigned batch sample). To ensure similar conditions existed during each test day, mode of transportation and consumption of drinks (water, coffee/tea without milk/sugar) before and during the first test were recorded and repeated at each subsequent test.

Questions on satiety were then asked on a regular basis post consumption until immediately prior to consumption of an ad libitum meal of a tomato and mozzarella pasta bake. Participants were given 30 minutes to consume the lunch and were instructed to eat only until they were comfortably full. Immediately post consumption of the lunch, questionnaires on satiety and liking were completed. Energy consumed at the meal was measured by a determination of the mass of food eaten.

Multiple questions relating to satiety were asked of the participants, and responses were scored and entered, at least every 30 minutes, before and after breakfast consumption, before and after consumption of the assigned batch sample, before and after an ad libitum meal. Statistical analysis was applied to the scores and a p value of lower than 0.05 was considered to be significant.

The four batch samples (300 mL Batch X, 300 mL Batch Z, 300 mL Batch 1, and 150 mL Batch 1) received comparable smell, taste, texture, and overall responses, thus differences in perceptions of hunger or fullness (discussed below) were not affected by the participants opinion of the sample itself.

Both Comparative Batch Z and inventive 300 mL Batch 1 received statistically significant scores in response to "how hungry do you feel?," and "how full do you feel?," after consumption of the assigned batch sample until the ad libitum meal 120 minutes later. In other words, the participants receiving Comparative Batch Z and inventive 300 mL Batch 1 felt less hungry over 120 minutes, and felt fuller for a more prolonged period of time. However, surprisingly in view of the similar responses, only the inventive Batch 1 at 300 mL dosage displayed a statistically significant reduction of energy intake at the ad libitum meal. Approximately 115-kcal reduction was achieved by consuming inventive Batch 1 at 300 mL dosage, equivalent to a 13% reduction of energy intake at the meal following consumption of the assigned batch sample.

Example 5

To demonstrate gelling and clearance of Batch A in the stomachs of human volunteers, a clinical study using Magnetic Resonance Imaging (MRI) is performed. The study design is reviewed by a certified Institutional Review Board and is conducted in accordance with International Conference on Harmonization/Good Clinical Practice standards.

Comparative Batches M and N are a conventional methylcellulose (METHOCEL A4M methylcellulose) and a blend of conventional methylcelluloses (55% METHOCEL SGA16M methylcellulose and 45% METHOCEL SGA7C methylcellulose) respectively selected to have closely matching initial solution viscosities with Inventive Batch A. Formulations are reported in Table 4, in weight percent:

TABLE 4

|  | Comparative Batch M | Comparative Batch N | Inventive Batch 2 |
|---|---|---|---|
| METHOCEL A4M methylcellulose | 2.0 | — | — |
| 55% METHOCEL SGA16M methylcellulose and 45% METHOCEL SGA7C methylcellulose | — | 2.0 | — |
| Batch A methylcellulose | — | — | 2.0 |
| Caramel | 0.25 | 0.25 | 0.25 |
| Sweetener (Sucofin, contains Maltodextrin and Aspartam) | 0.5 | 0.5 | 0.5 |
| Mint Oil | 1 drop/ 650 ml | 1 drop/ 650 ml | 1 drop/ 650 ml |
| Water | Q.S. | Q.S. | Q.S. |

$T_{gel}$ for METHOCEL A4M methylcellulose is 55° C.
$T_{gel}$ for METHOCEL SGA16M methylcellulose and METHOCEL SGA7C methylcellulose are each 38-44° C.
$T_{gel}$ for Batch A methylcellulose is 28° C.

For Batch 2, a 650 mL solution is made by adding the methylcellulose to water at room temperature stiffing at 500 rpm (IKA-overhead stirrer-propeller), then cooling to about 2.5° C. for 6 hours (the speed of the stirrer is reduced stepwise: 500 rpm for 15 min, then 400 rpm for 10 min, then 200 rpm for 10 min, and then 100 rpm for 5 h). Flavors are added with stirring at about 700 rpm with lab stirrer system (IKA Eurostar 6000 with propeller) in a ice-water bath, and stored in a refrigerator at about 0-2° C. overnight to de-gas.

For Comparative Batches M and N, 650 mL solutions are made by adding the methylcellulose to stiffing water at 40-50° C. at 800 rpm (IKA-overhead stirrer-propeller), then stiffing at 500 rpm for 15 min, cooling to about 2.5° C. for 90 min. Flavors are added with stiffing at about 700 rpm with lab stirrer system (IKA Eurostar 6000 with propeller) in a ice-water bath, and stored in a refrigerator at about 0-2° C. overnight to de-gas.

Samples are weighed into 300 mL aliquots and frozen until being thawed and used.

In a 3-way randomized, double-blind, crossover study, 6 participants attend on 3 different occasions approximately 1 week apart. MRI is carried out on a 3 T Philips Achieva MRI scanner. A range of MRI sequences (both $T_1$ and $T_2$ weighted and $T_2$ mapping) is used. Each volunteer is positioned supine in the scanner with a SENSE body coil wrapped up around the abdomen. Multislice, $T_2$-weighted axial images of the gastric contents are taken at intervals as well as single-slice, quantitative $T_2$ mapping of the gastric contents. Each image set is acquired on a short breath hold. Commercial software (Analyze 6, Biomedical Imaging Resources, Mayo Clinic, Rochester, Minn.) is used to trace manually around the region of interest on each slice. Volumes and $T_2$ values are calculated, and used to track formation and clearance of the gel from the stomach.

Participants are initially scanned at fasting to ensure the stomach is empty. They are then fed 300 mL of one of three different batches. The participants are then imaged at intervals for up to 4 hours to study the dynamics of gel formation. A 500 mL water refill drink is given once the stomach appears empty and a final scan is taken to assess gel retention. Batch 2 is observed to gel in vivo. Comparative Batch M and N are observed to not gel.

It is understood that the present invention is not limited to the embodiments specifically disclosed and exemplified herein. Various modifications of the invention will be apparent to those skilled in the art. Such changes and modifications may be made without departing from the scope of the appended claims.

Moreover, each recited range includes all combinations and subcombinations of ranges, as well as specific numerals contained therein. Additionally, the disclosures of each patent, patent application, and publication cited or described in this document are hereby incorporated herein by reference, in their entireties.

The invention claimed is:

1. A method for inducing satiety in an individual in need thereof, comprising orally administering to said individual, a liquid methylcellulose that gels in the individual's stomach, wherein the liquid methylcellulose has an in vitro gel fracture force of at least 1.5 N after conditioning the liquid at 39.5° C. for 1 hour.

2. The method of claim 1, wherein the liquid contains at least 0.2 weight percent methylcellulose.

3. The method of claim 1, wherein the individual is a human, and the individual consumes greater than three grams of methylcellulose.

4. The method of claim 3, wherein the individual is obese.

5. The method of claim 3, wherein the individual is not obese.

6. The method of claim 1, wherein the methylcellulose gels after 45 minutes upon entering the stomach.

7. The method of claim 1 wherein the methylcellulose has an average degree of methoxyl substitution per anhydroglucose unit of about 1.47 to about 2.2.

8. The method of claim 1 wherein the methylcellulose is administered in combination with a protein.

9. The method of claim 2 wherein the liquid contains up to 2.1 weight percent methylcellulose.

10. The method of claim 1, wherein the gel fracture force is at least 4 N after conditioning the liquid at 39.5° C. for 1 hour.

11. The method of claim 10, wherein the gel fracture force is at least 6 N after conditioning the liquid at 39.5° C. for 1 hour.

12. The method of claim 1, wherein the administered liquid methylcellulose contains from 0.2 to 2.1 weight percent methylcellulose that gels in the individual's stomach, wherein the individual consumes greater than three grams of the methylcellulose and wherein the methylcellulose gels after 45 minutes upon entering the stomach.

13. The method of claim 1, wherein the methylcellulose is ingested as a solution that contains water and 0.2 to 2.1 weight percent methylcellulose, and the methylcellulose is selected such that the solution is liquid at room temperature before ingestion but gels at a temperature below about 37° C. in the stomach.

* * * * *